US006372256B2

(12) United States Patent
Jamiolkowski et al.

(10) Patent No.: US 6,372,256 B2
(45) Date of Patent: Apr. 16, 2002

(54) HYDROGELS CONTAINING ABSORBABLE POLYOXAAMIDES

(75) Inventors: Dennis D. Jamiolkowski, Long Valley; Rao S. Bezwada, Whitehouse Station, both of NJ (US)

(73) Assignee: Ethicon, Inc., Sommerville, NJ (US)

( * ) Notice: Subject to any disclaimer, the term of this patent is extended or adjusted under 35 U.S.C. 154(b) by 0 days.

(21) Appl. No.: 09/847,788

(22) Filed: May 2, 2001

Related U.S. Application Data

(63) Continuation of application No. 09/365,449, filed on Aug. 2, 1999, now Pat. No. 6,251,435, which is a division of application No. 08/744,609, filed on Nov. 6, 1996, now Pat. No. 5,962,023, which is a continuation-in-part of application No. 08/611,532, filed on Mar. 5, 1996, now Pat. No. 5,597,579, which is a continuation-in-part of application No. 08/598,362, filed on Feb. 8, 1996, now abandoned, which is a continuation-in-part of application No. 08/554,614, filed on Nov. 6, 1995, now abandoned, which is a continuation-in-part of application No. 08/399,308, filed on Mar. 6, 1995, now Pat. No. 5,464,929.

(51) Int. Cl.$^7$ .................................................. A61K 9/14
(52) U.S. Cl. ...................... 424/486; 424/422; 424/423; 424/426; 424/484; 528/272
(58) Field of Search .............................. 424/422, 423, 424/426, 443, 444, 484, 486; 428/35.7

(56) References Cited

U.S. PATENT DOCUMENTS 4,510,295 A * 4/1985 Benzwada et al. .......... 525/437
4,546,152 A * 10/1985 Koelmel et al. ............ 525/437
5,464,929 A * 11/1995 Benzwada et al. .......... 528/361
5,597,579 A * 1/1997 Benzwada et al. .......... 424/426
5,645,850 A * 7/1997 Benzwada et al. .......... 424/426
6,187,095 B1 * 2/2001 Labrecque et al. ......... 118/110

* cited by examiner

*Primary Examiner*—Thurman K. Page
*Assistant Examiner*—Liliana Di Nola-Baron

(57) ABSTRACT

The present invention describes a crosslinked aliphatic polyoxaamide polymer and blends thereof that may be used to produce hydrogels, surgical devices such as catheters, molded devices, and the like. The crosslinked aliphatic polyoxaamide of the present invention are formed by crosslinking an aliphatic polyoxaamide having a first divalent repeating unit of formula I:

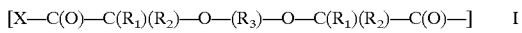

$$[X-C(O)-C(R_1)(R_2)-O-(R_3)-O-C(R_1)(R_2)-C(O)-] \quad I$$

and a second repeating unit selected from the group of formulas consisting of:

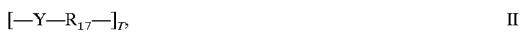

$$[-Y-R_{17}-]_P \quad II$$

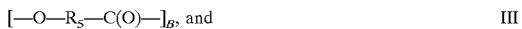

$$[-O-R_5-C(O)-]_B, \text{ and} \quad III$$

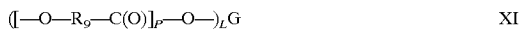

$$([-O-R_9-C(O)]_P-O-)_L G \quad XI$$

and combinations thereof, wherein X and Y are selected from the group consisting of —O— and —N(R)—, provided both X and Y are not both —O— and may be blended with a second polymer that is preferably biocompatible.

1 Claim, No Drawings

HYDROGELS CONTAINING ABSORBABLE POLYOXAAMIDES

FIELD OF THE INVENTION

The present invention is a continuation of Ser. No. 09/365,449, now U.S. Pat. No. 6,251,435 B1 filed Aug. 2, 1999, which is a divisional of Ser. No. 08/744,609 now U.S. Pat. No. 5,962,023, filed Nov. 6, 1996 which is a continuation-in-part of Ser. No. 08/611,532, now U.S. Pat. No. 5,597,579, filed Mar. 5, 1996, which is a continuation-in-part of Ser. No. 08/598,362, filed Feb. 8, 1996, now abandoned, which is a continuation-in-part of Ser. No. 08/554,614, filed Nov. 6, 1995, now abandoned, which is a continuation-in-part of Ser. No. 08/399,308, filed Mar. 6, 1995, now U.S. Pat. No. 5,464,929 (all hereby incorporated by reference herein) and relates to a polymeric material and more particularly to absorbable products made from polyoxaamides and blends thereof with wither polymers.

BACKGROUND OF THE INVENTION

Since Carothers early work in the 1920s and 1930s, aromatic polyester particularly poly(ethylene terephthalate) have become the most commercial important polyesters. The usefulness of these polymers is intimately linked to the stiffening action of the p-phenylene group in the polymer chain. The presence of the p-phenylene group in the backbone of the polymer chain leads to high melting points and good mechanical properties especially for fibers, films and some molded products. In fact poly(ethylene terephthalate) has become the polymer of choice for many common consumer products, such as one and two liter soft drink containers.

Several related polyester resins have been described in U.S. Pat. Nos. 4,440,922, 4,552,948 and 4,963,641 which seek to improve upon the properties of poly(ethylene terephthalate) by replacing terephthalic acid with other related dicarboxylic acids which contain phenylene groups. These polymers are generally designed to reduce the gas permeability of aromatic polyesters.

Other aromatic polyesters have also been developed for specialty applications such as radiation stable bioabsorbable materials. U.S. Pat. Nos. 4,510,295, 4,546,152 and 4,689,424 describe radiation sterilizable aromatic polyesters which can be used to make sutures and the like. These polymers like, poly(ethylene terephthalate), have phenylene groups in the backbone of the polymers.

However, less research has been reported on aliphatic polyesters. After Carothers initial work on polyesters, aliphatic polyesters were generally ignored because it was believed that these materials had low melting points and high solubilities. The only aliphatic polyesters that have been extensively studied are polylactones such as polylacride, polyglycolide, poly(p-dioxanone) and polycaprolactone. These aliphatic polylactones have been used primarily for bioabsorbable surgical sutures and surgical devices such as staples. Although polylactones have proven to be useful in many applications they do not meet all the needs of the medical community. For example films of polylactones do not readily transmit water vapor, therefore, are not ideally suited for use as bandages where the transmission of water vapor would be desired.

Only recently has there been renewed interest in non-lactone aliphatic polyesters. U.S. Pat. No. 5,349,028 describes the formation of very simple aliphatic polyesters based on the reaction of a dial with a dicarboxylic acid to form prepolymer chains that are then coupled together. These polyesters are being promoted for use in fibers and molded articles because these polyesters are biodegradable after they are buried such as in a landfill. However, these materials are not disclosed as being suitable for use in surgical devices.

Thus it is an object of the present invention to provide crosslinked aliphatic polyoxaamides (which includes polyoxaesteramides) and blends thereof with other polymers that may be used in surgical devices such as sutures, molded devices, drug delivery matrices, coatings, lubricants and the like.

SUMMARY OF THE INVENTION

We have discovered a new class of synthetic crosslinked polyoxaamides and blends thereof with other polymers that may be used to produce a variety of useful products including surgical devices such molded devices, drug delivery matrices, coatings, lubricants and the like. The crosslinked polyoxaamide polymers of the present invention are polymers comprising a first divalent repeating unit of formula I:

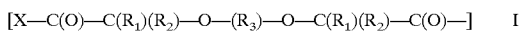

and a second repeating unit selected from the group of formulas consisting of:

and combinations thereof, wherein X and Y are selected from the group consisting of —O— and —N(R)—, provided that X and Y cannot both be —O—; R, $R_1$ and $R_2$ are independently selected from the group consisting of hydrogen and an alkyl group containing 1 to 8 carbon atoms; $R_3$ is selected from the group consisting of an alkylene unit and an oxyalkylene group of the following formula:

wherein C is an integer in the range of from 2 to about 5, D is an integer in the range of from 0 to about 2,000, and E is an integer in the range of from about 2 to about 5, except when D is zero, in which case E will be an integer in the range of from 2 to about 12; $R_{17}$ is a alkylene unit containing from 2 to 8 carbon atoms which may have substituted therein an internal ether oxygen, an internal —N($R_{18}$)— or an internal —C(O)—N($R_{21}$)—; T is an integer in the range of from 1 to about 2,000 and preferably is in the range of from 1 to about 1,000; $R_{18}$ and $R_{21}$ are independently selected from the group consisting of hydrogen and an alkyl group containing 1 to 8 carbon atoms; $R_5$ and $R_9$ are selected from the group consisting of —C($R_6$)($R_7$)—, —(CH$_2$)$_3$—O—, —CH$_2$—CH$_2$—O—CH$_2$—, —CR$_8$H—CH$_2$—, —(CH$_2$)$_5$—, —(CH$_2$)$_F$—O—C(O)— and —(CH$_2$)$_K$—C(O)—CH$_2$—; $R_6$ and $R_7$ are independently selected from the group consisting of hydrogen and an alkyl containing from 1 to 8 carbon atoms; $R_8$ is selected from the group consisting of hydrogen and methyl; F and K are independently selected integer in the range of from 2 to 6; B is an integer in the range of from 1 to n such that the number average molecular weight of formula III is less than about 200,000, preferably less than 100,000 and more preferably less than 40,000; P is an integer in the range of from 1 to m such that the number average molecular weight of formula XI is less than about 1,000,000, preferably less than 200,000 and more preferably less than 40,000; G represents the residue minus from 1 to L hydrogen atoms from the hydroxyl groups of an alcohol previously containing from 1 to about 200 hydroxyl groups; and L is an integer from about 1 to about 200; which have been crosslinked.

Additionally, the present invention describes a prepolymer comprising an aliphatic polyoxaamide chemically linked to at least one polymerizable region.

DETAILED DESCRIPTION OF THE INVENTION

The aliphatic polyoxaamides (which also includes polyoxaesteramides that are within the scope of the present invention) of the present invention are the reaction product of 1) an aliphatic polyoxydicarboxylic acid and a diamine or amino alcohol optionally containing one of the following compounds: a diol (or polydiol), a lactone (or lactone oligomer), a coupling agent or combination thereof.

Suitable aliphatic alpha-oxydicarboxylic acids (or oxadicarboxylic acids) for use in the present invention generally have the following formula:

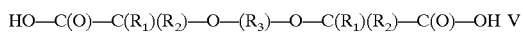
HO—C(O)—C($R_1$)($R_2$)—O—($R_3$)—O—C($R_1$)($R_2$)—C(O)—OH    V wherein R, $R_1$ and $R_2$ are independently selected from the group consisting of hydrogen and an alkyl group containing from 1 to 8 carbon atoms and $R_3$ is an alkylene containing from 2 to 12 carbon atoms or is an oxyalkylene group of the following formula:

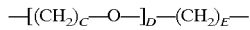
—[($CH_2$)$_C$—O—]$_D$—($CH_2$)$_E$—    IV wherein C is an integer in the range of from about 2 to about 5, D is an integer in the range of from 0 to about 2,000 and preferably 1 to about 12, and E is an integer in the range of from about 2 to about 5, except when D is zero, in which case E will be an integer in the range of from 2 to 12. These aliphatic alpha-oxydicarboxylic acids may be formed by reacting a diol or polydiol with an alpha-halocarboxylic acid such bromoacetic acid or chloroacetic acid under suitable conditions.

In some instances the corresponding mono or diester of the aliphatic alpha-oxydicarboxylic acids of formula V may be used.

Suitable amino alcohols, diamines, diols or polydiols for use in the present invention have repeating units with up to 8 carbon atoms having the formulas:

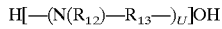
H[—(N($R_{12}$)—$R_{13}$—)$_U$]OH    VIA

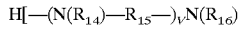
H[—(N($R_{14}$)—$R_{15}$—)$_V$N($R_{16}$)    VIB

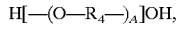
H[—(O—$R_4$—)$_A$]OH,    VIC

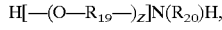
H[—(O—$R_{19}$—)$_Z$]N($R_{20}$)H,    VID wherein $R_{13}$, $R_{15}$, $R_4$ and $R_{19}$ are independently alkylene units containing from 2 to 8 methylene units which may have substituted therein an internal ether oxygen, an internal —N($R_{18}$)— or internal —C(O)—N($R_{21}$)—; $R_{18}$ and $R_{21}$ are independently selected from the group consisting of hydrogen and an alkyl group containing 1 to 8 carbon atoms; $R_{12}$, $R_{14}$, $R_{16}$ and $R_{20}$ are independently selected from the group consisting of hydrogen, alkyl group containing from 1 to 8 carbon atoms and mixtures thereof; A, U, V and Z are independently integers in the range of from 1 to about 2,000 and preferably from 1 to 1,000. Examples of suitable amino alcohols include amino alcohols selected from the group consisting of ethanol amine, isopropanol amine, 3-amino-1-propanol, 4-amino-1-butanol, 4-amino-2-butanol, 2-amino-1-butanol and 2-(2-aminoethoxy)ethanol. Examples of suitable diamines include diamines selected from the group consisting of ethylene diamine, 1,2-diaminopropane, 1,3-diaminopropane, 1,4-diaminobutane, 1,4-diaminocyclohexane and 1,5-diamino-3-oxapentane. Examples of suitable diols include diols selected from the group consisting of 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof. Examples of preferred polydiols include polydiols selected from the group consisting of polyethylene glycol (H[—O—$CH_2$—$CH_2$—]$_A$OH) and polypropylene glycol (H[—O—$CH_2$—CH($CH_3$)—]$_A$OH).

The polymer produced by reacting the aliphatic dioxacarboxylic acid with the amino alcohols discussed above should provide a polymer generally having the formula:

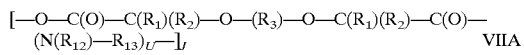
[—O—C(O)—C($R_1$)($R_2$)—O—($R_3$)—O—C($R_1$)($R_2$)—C(O)—
(N($R_{12}$)—$R_{13}$)$_U$—]$_J$    VIIA wherein $R_1$, $R_2$, $R_3$, $R_{12}$, $R_{13}$ and U are as described above; and J is an integer in the range of from about 1 to about 10,000 and preferably is in the range of from about 10 to about 1,000 and most preferably in the range of from about 50 to about 200.

The polymer produced by reacting the aliphatic dioxacarboxylic acid with the diamine discussed above should provide a polymer generally having the formula:

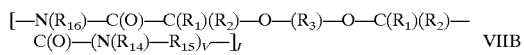
[—N($R_{16}$)—C(O)—C($R_1$)($R_2$)—O—($R_3$)—O—C($R_1$)($R_2$)—
C(O)—(N($R_{14}$)—$R_{15}$)$_V$—]$_J$    VIIB wherein $R_1$, $R_2$, $R_3$, $R_{14}$, $R_{15}$, $R_{16}$ V and J are as described above.

The polymer produced by reacting the aliphatic dioxacarboxylic acid with a mixture of aminoalcohols, diols and diamines discussed above should provide a polymer generally having end groups that may be active amines or hydroxyl groups.

Suitable lactone monomers that may be used in the present invention generally have the formula:

O—$R_5$—C(O)    VIII

These lactone monomers (or equivalent acids if any) may be polymerized to provide polymers of the following general structures:

H[—O—$R_5$—C(O)—]$_B$OH    IX

(H[—O—$R_9$—C(O)]$_P$—O—)$_L$G    X wherein $R_5$ and $R_9$ are independently selected from the group consisting of —C($R_6$)($R_7$)—, —($CH_2$)$_3$—O—, —$CH_2$—$CH_2$—O—$CH_2$—, —C$R_8$H—$CH_2$—, —($CH_2$)$_5$—, —($CH_2$)$_F$—O—C(O)— and —($CH_2$)$_K$—C(O)—$CH_2$—; $R_6$ and $R_7$ are independently selected from the group consisting of hydrogen and an alkyl containing from 1 to 8 carbon atoms; $R_8$ is selected from the group consisting of hydrogen and methyl; F and K are integers in the range of from 2 to 6; B is an integer in the range of from 1 to n such that the number average molecular weight of formula IX is less than about 200,000, preferably less than about 100,000, more preferably less than about 40,000 and most preferably less than 20,000; P is an integer in the range of from 1 to m such that the number average molecular weight of formula X is less than about 1,000,000, preferably less than about 200,000, more preferably less than about 40,000 and most preferably less than 20,000; G represents the residue minus from 1 to L hydrogen atoms from the hydroxyl groups of an alcohol previously containing from 1 to about 200 hydroxyl groups; and L is an integer from about 1 to about 200. Preferably G will be the residue of a dihydroxy alcohol minus both hydroxyl groups. Suitable lactone-derived repeating units may be generated from the following monomers include but are not limited to lactone monomers selected from the group consisting of glycolide, d-lactide, l-lactide, meso-lactide, ε-caprolactone, p-dioxanone, trimethylene carbonate, 1,4-dioxepan-2-one, 1,5-dioxepan-2-one and combinations thereof.

The polymer formed by reacting the above described amino alcohols, diamines, and diol (or polydiol) VI with the appropriate aliphatic oxadicarboxylic acid or aliphatic polyoxadicarboxylic acid V may also be copolymerized in a secondary ring-opening polymerization with the lactone monomers XIII or in a condensation copolymerization with the lactone oligomers IX or X, described above to form a polymer generally of the formula:

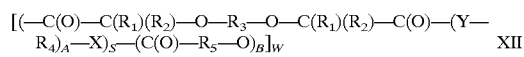

or

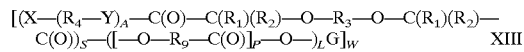

wherein X and Y are selected from the group consisting of —O— and N(R), provided that X and Y cannot both be —O—; and S is an integer in the range of from about 1 to about 10,000 and is preferably an integer in the range of from about 1 to about 1,000 and W is an integer in the range of from about 1 to about 1,000. These polymers may be made in the form of random copolymers or block copolymers. To the compounds described above there may be added a coupling agent selected from the group consisting of trifunctional or tetrafunctional polyols, oxycarboxylic acids, and polybasic carboxylic acids (or acid anhydrides thereof). The addition of the coupling agents causes the branching of long chains, which can impart desirable properties in the molten state to the polyester prepolymer. Examples of suitable polyfunctional coupling agents include trimethylol propane, glycerin, pentaerythritol, malic acid, citric acid, tartaric acid, trimesic acid, propane tricarboxylic acid, cyclopentane tetracarboxylic anhydride, triethanol amine and combinations thereof.

The amount of coupling agent to be added before gelation occurs is a function of the type of coupling agent used and the polymerization conditions of the polyoxaamide or molecular weight of the prepolymer to which it is added. Generally in the range of from about 0.1 to about 10 mole percent of a trifunctional or a tetrafunctional coupling agent may be added based on the moles of aliphatic polyoxaamide polymers present or anticipated from the synthesis.

The preparation of the aliphatic polyoxaamides (which also includes polyoxaesteramides) are preferably polymerizations performed under melt polycondensation conditions at elevated temperatures. At times it may be preferably to add a catalyst such as an organometallic compound. Preferred organometallic catalysts are tin-based catalysts e.g. stannous octoate. The catalyst will preferably be present in the mixture at a mole ratio of hydroxy groups, aliphatic polyoxadicarboxylic acid and optionally lactone monomer to catalyst will be in the range of from about 5,000 to about 80,000/1. The reaction is preferably performed at a temperature no less than about 120° C. under reduced pressure.

Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and the glass transition temperature and softening temperature of the polymer. The preferred reaction conditions of temperature, time and pressure can be readily determined by assessing these and other factors.

Generally, the reaction mixture will be maintained at about 220° C. The polymerization reaction can be allowed to proceed at this temperature until the desired molecular weight and percent conversion is achieved for the copolymer, which will typically take about 15 minutes to 24 hours. Increasing the reaction temperature generally decreases the reaction time needed to achieve a particular molecular weight, but may also increase the extent of side reactions. We have found that reaction at about 220° C. to be generally suitable.

An alternative method of preparing the aliphatic polyoxaamides involves the formation of a salt between the aliphatic alpha-oxydicarboxylic acids of the present invention and multifunctional amines(i.e. diamines) with susequent plymerization of the salt.

In another embodiment, aliphatic polyoxaamide copolymers can be prepared by forming an aliphatic polyoxaamide prepolymer polymerized under melt polycondensation conditions, then adding at least one lactone monomer or lactone prepolymer. The mixture would then be subjected to the desired conditions of temperature and time to copolymerize the prepolymer with the lactone monomers. If a lactone prepolymer is used, a polycondensation reaction can be used to increase the molecular weight.

The molecular weight of the prepolymer as well as its composition can be varied depending on the desired characteristic which the prepolymer is to impart to the copolymer. However, it is preferred that the aliphatic polyoxaamide prepolymers from which the copolymer is prepared have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the aliphatic polyoxaamide prepolymers described herein can also be made from mixtures of more than one diol, amino alcohol, or dioxacarboxylic acid.

One of the beneficial properties of the aliphatic polyoxaamide made by the process of this invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the aliphatic dioxacarboxylic acid and the diol for the formation of the aliphatic polyoxaamide prepolymer, it is preferable that the reaction mixture does not contain a concentration of any co-reactant which would render the subsequently prepared polymer nonabsorbable. Preferably, the reaction mixture is substantially free of any such co-reactants if the resulting polymer is rendered nonabsorbable.

These aliphatic polyoxaamides of the present invention and those described in Ser. No. 08/399,308, filed Mar. 6, 1995 and assigned to Ethicon, now U.S. Pat. No. 5,464,929 may be blended together with other homopolymers copolymers and graft copolymers to impart new properties to the material formed by the blend. The other polymers which the aliphatic polyoxaamides may be blended with include but are not limited to homopolymer and copolymer of lactone type polymers with the repeating units described by Formula VIII, polyesters (such as adipates) aliphatic polyurethanes, polyether polyurethanes, polyester polyurethanes, polyethylene copolymers (such as ethylene-vinyl acetate copolymers and ethylene ethyl acrylate copolymers), polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate) absorbable polyoxalates, absorbable polyanhydrides and combinations thereof. The copolymers (i.e. containing two or more repeating units) including random, block and segmented copolymers. Suitable lactone-derived repeating units may be generated from the following monomers include but are not limited to lactone monomers selected from the group consisting of glycolide, d-lactide, l-lactide, meso-lactide, ε-caprolactone, p-dioxanone, trimethylene carbonate, 1,4-dioxepan-2-one, 1,5-dioxepan-2-one and combinations thereof. The blends may contain about 1 weight percent to about 99 weight percent of the aliphatic polyoxaamides.

For some applications it may be desirable to add additional ingredients such as stabilizers, antioxidants radiopacifiers, fillers or the like.

The aliphatic polyoxaamide and other polymers may be blended using conventional mixing processes known in the art. For example a blend- can be prepared using a two-roll mill, an internal mixer (such as a Brabender or Banbury mixer), an extruder (such as a twin screw extruder) or the like.

The polymers and blends of this invention can be melt processed by numerous methods to prepare a vast array of useful devices. These polymer and blends can be injection or compression molded to make implantable medical and surgical devices, especially wound closure devices. The preferred wound closure devices are surgical clips, staples and sutures.

Alternatively, the polymers and blends can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for typing up and supporting damaged surface abrasions, particularly major abrasions, or areas where the skin and underlying tissues are damaged or surgically removed.

Additionally, the polymers and blends can be molded to form films which, when sterilized, are useful as adhesion prevention barriers. Another alternative processing technique for the polymers and blends of this invention includes solvent casting, particularly for those applications where a drug delivery matrix is desired.

In more detail, the surgical and medical uses of the filaments, films, and molded articles of the present invention include, but are not necessarily limited to:

Knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. suture knot clip
j. orthopedic pins, clamps, screws, and plates
k. clips (e.g.,for vena cava)
l. staples
m. hooks, buttons, and snaps
n. bone substitutes (e.g., mandible prosthesis)
o. intrauterine devices (e.g.,spermicidal devices)
p. draining or testing tubes or capillaries
q. surgical instruments
r. vascular implants or supports
s. vertebral discs
t. extracorporeal tubing for kidney and heart-lung machines
u. artificial skin and others
v. catheters (including, but not limited to, the catheters described in U.S. Pat. No. 4,883,699 which is hereby incorporated by reference)
w. scaffoldings and the like for tissue engineering applications.

In another embodiment, the polymers and blends (which includes prepolymers and suitable crosslinked polymers) can be used to coat a surface of a surgical article to enhance the lubricity of the coated surface. The polymer blends may be applied as a coating using conventional techniques. For example, the polymers and blends may be solubilized in a dilute solution of a volatile organic solvent, e.g. acetone, methanol, ethyl acetate or toluene, and then the article can be immersed in the solution to coat its surface. Once the surface is coated, the surgical article can be removed from the solution where it can be dried at room or elevated temperatures until the solvent and any residual reactants are removed.

For use in coating applications the polymers and blends should exhibit an inherent viscosity (in the case of crosslinked polymers before crosslinking), as measured in a 0.1 gram per deciliter (g/dl) of hexafluoroisopropanol (HFIP), between about 0.05 to about 2.0 dl/g, preferably about 0.10 to about 0.80 dl/g. If the final inherent viscosity were less than about 0.05 dl/g, then the polymers and blends may not have the integrity necessary for the preparation of films or coatings for the surfaces of various surgical and medical articles. On the other hand, although it is possible to use polymers and blends with an inherent viscosity (for crosslinkable polymers measured before crosslinking) greater than about 2.0 dl/g, it may be exceedingly difficult to do so.

Although it is contemplated that numerous surgical articles (including but not limited to endoscopic instruments) can be coated with the polymers and blends of this invention to improve the surface properties of the article, the preferred surgical articles are surgical sutures and needles. The most preferred surgical article is a suture, most preferably attached to a needle. Preferably, the suture is a synthetic absorbable suture. These sutures are derived, for example, from homopolymers and copolymers of lactone monomers such as glycolide, lactide, ε-caprolactone, 1,4-dioxanone, and trimethylene carbonate. The preferred suture is a braided multifilament suture composed of polyglycolide or poly (glycolide-co-lactide).

The amount of polymer or blend to be applied on the surface of a braided suture can be readily determined empirically, and will depend on the particular copolymer and suture chosen. Ideally, the amount of polymer blend applied to the surface of the suture may range from about 0.5 to about 30 percent of the weight of the coated suture, more preferably from about 1.0 to about 20 weight percent, most preferably from 1 to about 5 weight percent. If the amount of coating on the suture were greater than about 30 weight percent, then it may increase the risk that the coating may flake off when the suture is passed through tissue.

Sutures coated with the polymers and blends of this invention are desirable because they have a more slippery feel, thus making it easier for the surgeon to slide a knot down the suture to the site of surgical trauma. In addition, the suture can be passed more easily through body tissue thus reducing tissue trauma. These advantages are exhibited in comparison to sutures which do not have their surfaces coated with the polymers and blends of this invention.

In another embodiment of the present invention when the article is a surgical needle, the amount of coating applied to the surface of the article is an amount which creates a layer with a thickness ranging preferably between about 2 to about 20 microns on the needle, more preferably about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In yet another embodiment of the present invention, the polymers and blends can be used as a pharmaceutical carrier in a drug delivery matrix. To form this matrix the polymers and blends would be mixed with a therapeutic agent to form the matrix. The variety of different therapeutic agents which can be used in conjunction with the polymers and blends of the present invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form such as oral, parenteral, a subcutaneously as an implant, vaginally or as a suppository. Matrix formulations containing the polymer blends may be formulated by mixing one or more therapeutic agents with the blends. The therapeutic agent, may be present as a liquid, a finely divided solid, or any other appropriate physical form. Typically, but optionally, the matrix will include one or more additives, e.g., nontoxic auxiliary substances such as diluents, carriers, excipients, stabilizers or the like. Other suitable additives may be formulated with the polymers and blends and pharmaceutically active agent or compound, however, if water is to be used it should be added immediately before administration.

The amount of therapeutic agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of polymers and blends incorporated into the parenteral will vary depending on the release profile desired and the amount of drug employed. The product may contain blends of polymers of different molecular weights to provide the desired release profile or consistency to a given formulation.

The polymers and blends, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (over, say 1 to 2,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drugs and polyoxaamide containing polymers may be tested in appropriate in vitro and in vivo models to achieve the desired drug release profiles. For example, a drug could be formulated with a polyoxaamide and orally administered to an animal. The drug release profile could then be monitored by appropriate means such as, by taking blood samples at specific times and assaying the samples for drug concentration. Following this or similar procedures, those skilled in the art will be able to formulate a variety of formulations.

The polymers (including copolymers) and blends of the present invention can be crosslinked to affect mechanical properties. Crosslinking may either be chemically or physical. Chemically crosslinked polymer chains are connected by covalent bonds, which can be formed by reactive groups contained on the polymers, the addition of crosslinking enhancers and/or irradiation (such as gamma-irradiation). Physical crosslinking on the other hand connects the polymer chains through non-covalent bonds such as van der Waals interactions, hydrogen bonding or hydrophobic interactions. In particular, crosslinking can be used to control the water swellability of said invention.

In one embodiment, Formulas VII A and VII B may be endcapped with one or more crosslinkable regions.

Similarly, Formula XII and XIII may be crosslinked by attaching one or more polymerizable regions to an amine group.

The polymerizable regions are preferably polymerizable by photoinitiation by free radical generation, most preferably in the visible or long wavelength ultraviolet radiation. The preferred polymerizable regions are acrylates, diacrylates, oligoacrylates, methacrylates, dimethacrylates, oligomethoacrylates, or other biologically acceptable photopolymerizable groups.

Other initiation chemistries may be used besides photoinitiation. These include, for example, water and amine initiation schemes with isocyanate or isothiocyanate containing macromers used as the polymerizable regions.

Useful photoinitiaors are those which can be used to initiate by free radical generation polymerization of the macromers without cytotoxicity and within a short time frame, minutes at most and most preferably seconds. Preferred dyes as initiators of choice for long wave length ultraviolet (LWUV) or visible light initiation are ethyl eosin, 2,2-dimethoxy-2-phenyl acetophenone, other acetophenone derivatives, and camphorquinone. Crosslinking and polymerization may be initiated among macromers by a light activated free-radical polymerization initiator such as 2,2-dimethoxy-2-phenyl acetophenone, other acetophenone derivatives, and camphorquinone. In other cases, crosslinking and polymerization are initiated among macromers by a light-activated free-radical polymerization initiator such as 2,2-dimethoxy-2-phenylacetophenone or a combination of ethyl eosin ($10^{-4}$ to $10^{-2}$M) and triethanol amine (0.001 to 0.1M), for example.

The choice of the photoinitiator is largely dependent on the photopolymerizable regions. Although we do not wish to be limited by scientific theory, it is believed that the macromer includes at least one carbon-carbon double bond, light absorption by the dye can cause the dye to assume a triplet state, the triplet state subsequently reacting with the amine to form a free radical which initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by LWUV light or by laser light of about 514 nm, for example.

Initiation of polymerization (crosslinking) is accomplished by irradiation with light at a wavelength of between about 200–700 nm, most preferably in the long wavelength ultraviolet range or visible range, 320 nm or higher, most preferably about 514 nm or 365 nm.

There are several photooxidizable and photoreductible dyes that may be used to initiate polymerization (crosslinking). These include acridine dyes, for example, acriblarine; thiazine dyes, for example, thionine; xanthine dyes, for example, rose bengal; and phenazine dyes, for example, methylene blue. These are used with cocatalysis such as amines, for example, triethanolamine; sulphur compounds, for example, $RSO_2R^1$; heterocycles, for example, imidazole; enolates; organometallics; and other compounds, such as N-phenyl glycine. Other initiators include camphorquinones and acetophenone derivatives.

Thermal polymerization initiator systems may also be used. Thermal initiators may be selected to allow polymerization to be initiated at a desired temperature. At times it may be desired to use a high temperature to initiate polymerization such as during a molding process. For many medical uses it will be desired to use systems that will initiate free radical polymerization at physiological temperatures include, for example, potassium persulfate, with or without tetramethyl ethylenediamine; benzoylperoxide, with or without triethanolamine; and ammonium persulfate with sodium bisulfite.

The crosslinked polymers (including copolymers) and blends (hereinafter polymers) can be processed and used for many of the same uses as described heretofor. In addition, crosslinked polymers are particularly well suited for the prevention of surgical adhesions, tissue adhesions, tissue coatings and in tissue engineering.

A preferred application is a method of reducing formation of adhesions after a surgical procedure in a patient. The method includes coating damaged tissue surfaces in a patient with an aqueous solution of a light-sensitive free-radical polymerization initiator and a macromer solution as described above. The coated tissue surfaces are exposed to light sufficient to polymerize the macromer. The light-sensitive free-radical polymerization initiator may be a single compound (e.g., 2,2-dimethoxy-2-phenyl acetophenone) or a combination of a dye and a cocatalyst (e.g., ethyl eosin and triethanol amine).

Additionally, the crosslinked polymers can also be used to form hydrogels which are a three dimensional network of hydrophilic polymers in which a large amount of water is present. In general the amount of water present in a hydrogel is at least 20 weight percent of the total weight of the dry polymer. The most characteristic property of these hydrogels is that it swells in the presence of water and shrinks in the absence of water.

The extent of swelling (equilibrium water content) is determined by the nature (mainly the hydrophilicity) of the polymer chains and the crosslinking density.

The kinetics of hydrogel swelling is limited by the diffusion of water through the outer layers of the dried hydrogel. Therefore, while hydrogels swell to a large extent in water, the time it takes to reach equilibrium swelling may be significant depending on the size and shape of the hydrogel. To reduce the amount of time it takes for a hydrogel to reach equilibrium, hydrogel foams may be used. Hydrogels foams may be made by crosslinking polymers in the presence of gas bubbles. The hydrogels foams prepared with macroscopic gas cells will have an open celled structure similar to sponges except that the pore size will generally be an order of magnitude larger.

Hydrogels may be used for many of same uses that have been described for polyoxaamides such as wound dressings materials, since the crosslinked hydrogels are durable, non-antigenic, and permeable to water vapor and metabolites, while securely covering the wound to prevent bacterial infection. Hydrogels may also be used for coatings in general and medical coatings in particular. The hydrogel coatings may provide a smooth slippery surface and prevent bacterial colonization on the surface of the medical instrument. For example hydrogels may be used as coatings on urinary catheter surfaces to improve its biocompatability. Hydrogels may also be used in a variety of applications where the mechanical swelling of the hydrogel is useful such as in catheters as a blend component with a biocompatable elastomer (such as the elastomer described in U.S. Pat. No. 5,468,253 hereby incorporated by reference). Additionally, hydrogels could be used for drug delivery or immobilization of enzyme substrates or cell encapsulization. Other uses for hydrogels have been described in the literature many of which are discussed in chapter one of *Hydrogels and Biodegradable Polymers for Bioapplications,* published by the Amercian Chemical Society (which is hereby incorporated by reference herein).

Crosslinking to form crosslinked structures can be performed in a variety of ways. For example the polymers may be crosslinked while being synthesized such as by utilizing a multifuncitonal monomers or oligomers. However, crosslinking at other times is also advantageous. For example crosslinking may be performed during the manufacture of a device such by adding a thermal initiator to the polymer prior to injection molding a device. Additionally, crosslinking of a polymerizable region with a photoinitiator may be performed during stereolithography to form devices. European Patent Application 93305586.5 describes the process for performing stereolithography (with photopolymerizable materials). As previously discussed photoinitiation may be used in viva to crosslink the polymers of the present invention for various wound treatments such as adhesion prevention and wound sealing. Coating may also be applied to devices and crosslinked in situ to form films that will conform to the surface of the device.

In a further embodiment of the present invention the polyoxaamide polymers, polymer blends, pre-crosslinked and post-crosslinked polymers of the present invention can be used in tissue engineering applications as supports for cells. Appropriate tissue scaffolding structures are known in the art such as the prosthetic articular cartilage described in U.S. Pat. No. 5,306,311, the porous biodegradable scaffolding described in WO 94/25079, and the prevascularized implants described in WO 93/08850 (all hereby incorporated by reference herein). Methods of seeding and/or culturing cells in tissue scaffoldings are also known in the art such as those methods disclosed in EPO 422 209 B1, WO 88/03785, WO 90/12604 and WO 95/33821 (all hereby incorporated by reference herein). Additionally, the crosslinkable pre-polymers of the present invention can be used to encapsulate cells for tissue engineering purposes.

The Examples set forth below are for illustration purposes only, and are not intended to limit the scope of the claimed invention in any way. Numerous additional embodiments within the scope and spirit of the invention will become readily apparent to those skilled in the art.

EXAMPLE 1

Preparation of 3,6-Dioxaoctanedioic Acid and its dimethylester

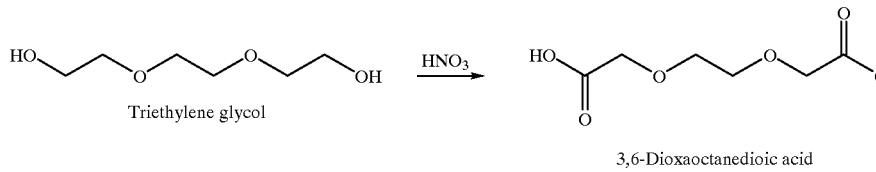
Triethylene glycol

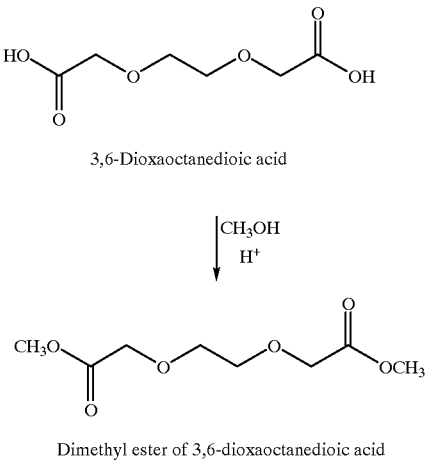
3,6-Dioxaoctanedioic acid

Dimethyl ester of 3,6-dioxaoctanedioic acid

The diacid, 3,6-dioxaoctanedioic acid, was synthesized by oxidation of triethylene glycol. The oxidation was carried out in a 500 milliliter, three-neck round bottom flask equipped with a thermometer, an additional funnel, a gas absorption tube and a magnetic spinbar. The reaction flask was lowered into an oil bath resting upon a magnetic stirrer. To the reaction flask was added 157.3 ml of a 60% nitric acid solution; 37.0 g of triethylene glycol was added to the additional funnel. The contents of the flask were heated to 78–80° C. A test tube containing 0.5 g of glycol and one milliliter of concentrated nitric acid was warmed in a water bath until brown fumes started appearing. The contents were then added to the reaction flask. The mixture was stirred for a few minutes; the glycol was then carefully added. The rate of addition had to be monitored extremely carefully to keep the reaction under control. The addition rate was slow enough so that the temperature of the exothermic reaction mixture was maintained at 78–82° C. After the addition was completed (80 minutes), the temperature of the reaction mixture was maintained at 78–80° C. for an additional hour. While continuing to maintain this temperature range, the excess nitric acid and water was then distilled off under reduced pressure (water suction). The syrupy residue was cooled; some solids appeared. The reaction product had the IR and NMR spectra expected for the dicarboxylic acid; the crude product was used as such for esterification.

The crude diacid could be purified to the extent needed for polymerization or alternately could be converted to the corresponding diester, the diester purified and subsequently hydrolyzed back to (purified) diacid. In yet another mode of purification, the diamine salts of the diacids are purified and then subsequently polymerized to form the polyoxaamides of the present invention.

Esterification of the crude 3,6-dioxaoctanedioic acid was accomplished as follows: To the reaction flask containing 36 g of the crude diacid, was added 110 ml of methanol. This was stirred for 3 days at room temperature after which 15 g of sodium bicarbonate was added and stirred overnight. The mixture was filtered to remove solids. To the liquor was added an additional 10 g of sodium bicarbonate; this mixture was stirred overnight. The mixture was again filtered; the liquor was fractionally distilled. NMR analysis of the esterified product showed a mixture of dimethyl triglycolate (78.4 mole %) and monomethyltriglycolate (21.6 mole %). No significant condensation of diacid was observed.

EXAMPLE 2

Preparation of polyoxaesteramide from 3,6-dioxaoctanedioic Acid and ethanolamine

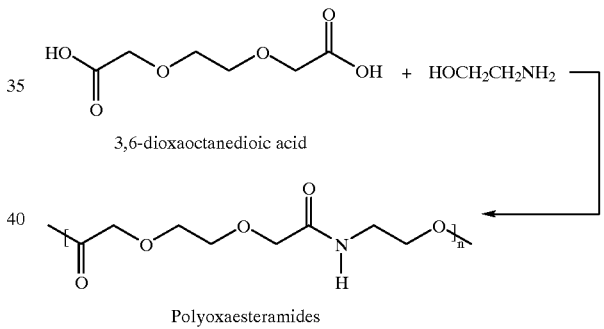
3,6-dioxaoctanedioic acid

Polyoxaesteramides

A flame dried, mechanically stirred, 50-milliliter glass reactor suitable for polycondensation reaction, is charged with the equivalent of 0.1 mole of purified 3,6-dioxaoctanedioic acid from Example 1 (17.81g), and 0.1 mole of ethanolamine (6.11 g). This generally could be done by charging the reactor with exact stoichometric amounts of the diacid and the amino alcohol; alternately a small excess of ethylene glycol can be substituted for a portion of the amino alcohol. The polymerization can be conducted without additional catalyst or alternately a small amount of catalyst (eg. 0.0606 ml of a solution of 0.33M stannous octoate in toluene) can be added. After purging the reactor and venting with nitrogen, the temperature is gradually raised over the course of 26 hours to 180°C. A temperature of 180° C. is then maintained for another 20 hours; all during these heating periods under nitrogen at one atmosphere, the water formed is collected. The reaction flask is allowed to cool to room temperature; it is then slowly heated under reduced pressure (0.015–1.0 mm) over the course of about 32 hours to 160° C., during which time additional distillates can be collected. A temperature of 160° C. is maintained for 4 hours after which a sample, a few grams in size, of the polymer formed is taken. The sample is found to have an inherent viscosity (I.V.) of approximately 0.2 dl/g, as determined in hexaflouroisopropanol (HFIP) at 25° C. at a concentration of 0.1 g/dl. The polymerization is continued under reduced pressure while raising the temperature, in the course of about 16 hours, from 160° C. to 180° C.; a temperature of 180° C. is maintained for an additional 8 hours, at which time a polymer sample is taken and found to have an I.V. of approximately 0.3 dl/g. The reaction is continued under reduced pressure for another 8 hours at 180° C. The resulting polymer should have an inherent viscosity of approximately 0.4 dl/g, as determined in HFIP at 25OC and at a concentration of 0.1 g/dl.

EXAMPLE 3

Preparation of polyoxaamide with 3,6,9-trioxaundecanedioic Acid and ethylene diamine ylene glycol can be substituted for a portion of the diamine. The polymerization can be conducted without additional catalyst or alternately a small amount of catalyst (eg. 0.0606 ml of a solution of 0.33M stannous octoate in toluene or 10 milligrams of dibutyltin oxide) can be added.

After purging the reactor and venting with nitrogen, the contents of the reaction flask are gradually heated under nitrogen at one atmosphere, in the course of about 32 hours, to 180° C., during which time the water formed is collected. The reaction mass is allowed to cool to room temperature. The reaction mass is then heated under reduced pressure (0.015–1.0 mm), gradually increasing the temperature to 180° C. in about 40 hours; during this time additional distillates is collected. The polymerization is continued under reduced pressure while maintaining 180° C. for an additional 16 hours. The resulting polymer should have an

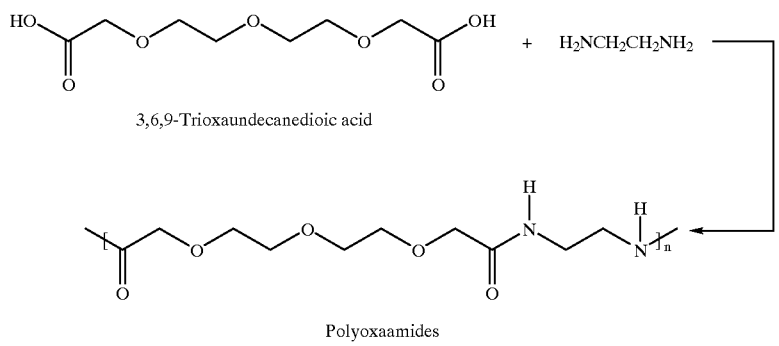

A flame dried, mechanically stirred, 250-milliliter glass reactor, suitable for polycondensation reaction, is charged with the equivalent of 0.2 mole (44.44 g) of 3,6,9-trioxaundecanedioic acid, and 0.2 mole (12.02 g) of ethylene diamine; this can be conveniently done by charging the reactor with the stoichometric salt formed between the diacid and the diamine. Alternately a small excess of ethinherent viscosity of approximately 0.5 dl/g as determined in HFIP at 25° C. and at a concentration of 0.1 g/dl.

EXAMPLE 4

Preparation of polyoxaamide with polyglycol diacid and Jeffamine

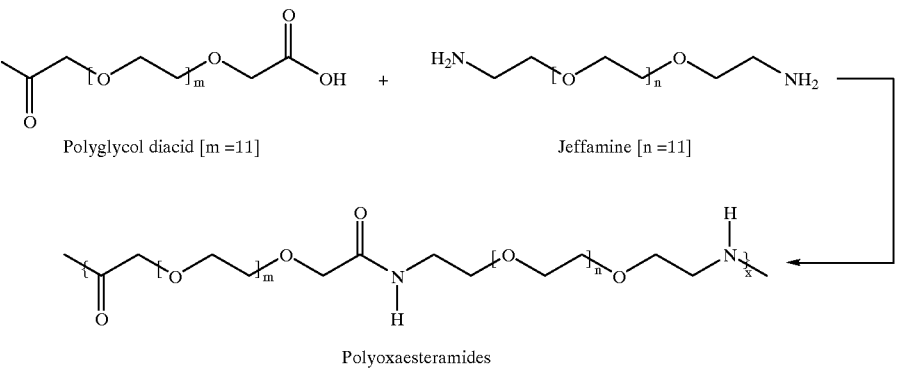

A flame dried, mechanically stirred, 500-milliliter glass reactor (suitable for polycondensation reaction) is charged with the equivalent of 0.2 mole (123.8 g) of polyglycol diacid (molecular weight about 619), and 0.2 mole (117.7g) of Jeffamine (amine terminated polyethylene oxide). This generally could be done by charging the reactor with stoichometric amounts of the diacid and the diamine or by charging the corresponding preformed salt of the diacid and diamine. As an alternate process, a small excess of ethylene glycol can be substituted for a portion of the diamine. The polymerization can be conducted without additional catalyst or alternately a small amount of catalyst. After purging the reactor and venting with nitrogen, the contents of the reaction flask is heated under nitrogen at one atmosphere, gradually increasing the temperature to 200° C. in about 32 hours; during this time the water formed is collected. The reaction flask is heated gradually under reduced pressure (0.015–1.0 mm) from room temperature to 140° C. in about 24 hours, during which time additional distillates are collected. A polymer sample of about ten grams is taken at this stage, and found to have an I.V. of approximately 0.1 dl/g in HFIP at 25° C., 0.1 g/dl. The polymerization is continued under reduced pressure while heating from 140° C. to 180° C. in about 8 hours, and then maintained at 180° C. for an additional 8 hours. The reaction temperature is then increased to 190° C. and maintained there under reduced pressure for an additional 8 hours. The resulting polymer should have an inherent viscosity of approximately 0.6 dl/g as determined in HFIP at 25° C. and at a concentration of 0.1 g/dl.

We claim:

1. A crosslinkable polyoxaamide prepolymer comprising a polyoxaamide having a first divalent repeating unit of formula I:

[X—C(O)—C($R_1$)($R_2$)—O—($R_3$)—O—C($R_1$)($R_2$)—C(O)—]   I and a second repeating unit selected from the group of formulas consisting of:

[—Y—$R_{17}$—]$_T$,   II

[—O—$R_5$—C(O)—]$_B$,   III ([—O—$R_9$—C(O)]$_P$—O—)$_L$G   XI and combinations thereof, wherein X and Y are selected from the group consisting of —O— and —N(R)—, provided that X and Y cannot both be —O—; R, $R_1$ and $R_2$ are independently selected from the group consisting of hydrogen and an alkyl group containing 1 to 8 carbon atoms; $R_3$ is selected from the group consisting of an alkylene unit and an oxyalkylene group of the following formula:

—[($CH_2$)$_C$—O—]$_D$—($CH_2$)$_E$—   IV wherein C is an integer in the range of from 2 to about 5, D is an integer in the range of from 0 to about 2,000, and E is an integer in the range of from about 2 to about 5, except when D is zero, in which case E will be an integer in the range of from 2 to 12; $R_{17}$ is an alkylene unit containing from 2 to 8 carbon atoms which may have substituted therein an internal ether oxygen, an internal —N($R_{18}$)— or an internal —C(O)—N($R_{21}$)—; T is an integer in the range of from 1 to 2,000; $R_{18}$ and $R_{21}$ are independently selected from the group consisting of hydrogen and an alkyl group containing 1 to 8 carbon atoms; $R_5$ and $R_9$ are selected from the group consisting of —C($R_6$)($R_7$)—, —($CH_2$)$_3$—O—, —$CH_2$—$CH_2$—O—$CH_2$—, —C$R_8$H—$CH_2$—, —($CH_2$)$_5$—, —($CH_2$)$_F$—O—C(O)— and —($CH_2$)$_K$—C(O)—$CH_2$—; $R_6$ and $R_7$ are independently selected from the group consisting of hydrogen and an alkyl containing from 1 to 8 carbon atoms; $R_8$ is selected from the group consisting of hydrogen and methyl; F and K are independently selected integer in the range of from 2 to 6; B is an integer in the range of from 1 to n such that the number average molecular weight of formula III is less than about 200,000; P is an integer in the range of from 1 to m such that the number average molecular weight of formula XI is less than about 1,000,000; G represents the residue minus from 1 to L hydrogen atoms from the hydroxyl groups of an alcohol previously containing from 1 to about 200 hydroxyl groups; and L is an integer from about 1 to about 200; having at least one polymerizable region s chemically linked to the polyoxaamide.

* * * * *